United States Patent [19]
Maeda et al.

[11] 3,993,699
[45] Nov. 23, 1976

[54] PROCESS FOR PRODUCING XYLYLENE GLYCOLS

[75] Inventors: Satoshi Maeda; Atsushi Kondo; Shinzi Nishimura, all of Tokyo, Japan

[73] Assignee: Hodogaya Chemical Co., Ltd., Tokyo, Japan

[22] Filed: Apr. 16, 1975

[21] Appl. No.: 568,659

[52] U.S. Cl. .................. 260/618 R; 260/488 CD
[51] Int. Cl.² ........................................ C07C 29/00
[58] Field of Search .............. 260/618 R, 488 CD

[56] References Cited
UNITED STATES PATENTS

| | | | |
|---|---|---|---|
| 2,939,886 | 11/1964 | Pritchard et al. | 260/488 CD |
| 3,158,645 | 6/1970 | Newcomer et al. | 260/488 CD |
| 3,557,222 | 1/1971 | Withers et al. | 260/618 R |

FOREIGN PATENTS OR APPLICATIONS

| | | | |
|---|---|---|---|
| 2,245,457 | 3/1973 | Germany | 260/488 |

OTHER PUBLICATIONS
Trautmann et al., J. Fur. Praktische Chemie, Band 313 pp. 561–568 (1971).

Primary Examiner—James O. Thomas, Jr.
Assistant Examiner—James H. Reamer
Attorney, Agent, or Firm—Cushman, Darby & Cushman

[57] ABSTRACT

A process for producing a xylylene glycol, which comprises reacting a xylylene dichloride with an alkali metal or alkaline earth metal salt of acetic acid using a tertiary amine as catalyst in the presence of an inert organic solvent to effect esterification, removing the by-product inorganic chloride and the catalyst from the organic solvent layer containing diacetoxymethylbenzene which was formed, adding to the resulting organic solvent layer an aqueous alkali solution to effect saponification, separating the aqueous solution layer containing xylylene glycol which was formed, and extracting said aqueous solution layer with an extraction solvent to recover the xylylene glycol.

9 Claims, No Drawings

PROCESS FOR PRODUCING XYLYLENE GLYCOLS

This invention relates to a process for producing a xylylene glycol. More particularly, it relates to a novel and improved process for producing a xylylene glycol by esterification of a xylylene dichloride used as the starting material to synthesize a diacetoxymethylbenzene which is then saponified to yield a corresponding xylylene glycol.

Xylylene glycols are useful as starting materials for the manufacture of polyester and polyurethane resins. There have heretofore been known two common methods for producing xylylene glycols starting from a xylylene dichloride: (1) direct hydrolysis of xylylene dichloride with a dilute aqueous alkali solution, and (2) a two-stage process which comprises reacting xylylene dichloride with an alkali metal or alkaline earth metal salt of acetic acid to yield diacetoxymethylbenzene which is then saponified with an alkali.

The first method of directly hydrolyzing xylylene dichloride has an advantage of producing xylylene glycol in single stage, but there is always formed a condensation product as an unavoidable by-product. Accordingly, various attempts have been made to diminish the formation of such a by-product. The proposals made so far include the hydrolysis at an elevated temperature and under a superatmospheric pressure, the hydrolysis in the presence of a surface active agent, and the hydrolysis while keeping the reacting mixture in a dispersion state by means of a high-speed rotary emulsifying machine or the like (Japanese Patent Publication No. 2,972/71). All of these attempts, however, are directed to the acceleration of the rate of hydrolysis, which will result in diminished formation of the by-product, and no success has ever been achieved in substantially eliminating the side reaction. Moreover, the direct hydrolysis of xylylene dichloride with an aqueous alkali solution generally requires so large a quantity of water that in order to recover xylylene glycol by recrystallization or solvent extraction after completion of the reaction, the dilute reaction solution containing a few percent of the glycol must be concentrated to a concentration of 15% or higher or even evaporated to dryness because of an extremely high solubility of the glycol in water. Concentrating such a large quantity of the reaction solution is an economical disadvantage of the process when carried out in a commercial scale.

The second method, which is a so-called two-stage process involving esterification of xylylene dichloride and succeeding saponification to yield xylylene glycol, has an advantage of not yielding by-products of the dibenzyl ether type. A known two stage procedure comprises heating xylylene dichloride and anhydrous sodium acetate in glacial acetic acid to form diacetoxymethylbenzene, separating the latter from the reaction mixture, converting it into xylylene glycol by hydrolysis with alcoholic potash, removing the precipitated potassium acetate by filtration, and concentrating the filtrate to precipitate xylylene glycol [Kobunshi Kagaku (a Japanese journal of high polymer chemistry) 9, 205–210 (1952)]. Another known procedure involves reacting xylylene dichloride with an aquous potassium acetate solution, hydrolyzing the resuling esterification mixture with an aqueus alkali solution, cooling the reaction mixture to precipitate xylylene glycol and the inorganic chloride which were formed, extracting the resulting crystalline mixture with an organic solvent to dissolve selectively xylylene glycol, and recovering the xylylene glycol from the solution thus obtained (U.S. Pat. No. 2,939,886). These procedures, however, require an autoclave in some cases depending upon the reaction conditions, also require a long period of time for the esterification stage, and, in view of the economical standpoint, do not yet reach a satisfiable level because of a low overall yield of xylylene glycol from xylylene dichloride.

There has been proposed an esterification method whereby benzyl benzoate is formed from benzyl chloride and sodium benzoate, which comprises using a tertiary amine as catalyst in the absence of a reaction medium, except for the reactants themselves [Ind. Eng. Chem., 38 (2), 207–211 (1946)]. The said literature, however, carries no information on the procedure for hydrolyzing the resulting esterification mixture to form the corresponding alcohol, then purifying and recovering said alcohol.

An object of this invention is to provide a novel and improved process for producing industrially useful xylylene glycols by specific combination of steps of esterification, saponification, purification and product recovery, thus eliminating the aforesaid disadvantages of the convertional processes.

The process of this invention for producing xylylene glycol comprises reacting xylylene dichloride with an alkali metal or alkaline earth metal salt of acetic acid using a tertiary amine as catalyst in the presence of an inert organic solvent to effect esterification, removing the by-product inorganic chloride and the catalyst from the organic solvent layer containing diacetoxymethylbenzene which was formed, adding an aqueous alkali solution to the resulting organic layer to effect saponification, separating the aqueous solution layer containing xylylene glycol which was formed, and extracting said aqueous solution layer with an extraction solvent to recover the xylylene glycol.

The xylylene dichloride to be used as the starting material in the process of this invention can be any of the o-, m-, and p-isomer and the corresponding o-, m-, or p-xylylene glycol can be formed therefrom. Two known general methods for producing xylylene dichloride are chloromethylation of benzene or benzyl chloride and side-chain chlorination of xylene. For example, the side-chain chlorination of p-xylene is advantageous in producing the p-isomer in high yields because no other isomer is formed. It is impossible, however, to obtain xylylene dichloride exclusively even by side-chain chlorination because by-products of different degree of chlorination, such as methylbenzyl chloride or dichloromethylbenzyl chloride, are simultaneously formed. Even after purification of the reaction solution obtained by chlorination of xylene, the xylylene dichloride which is obtained generally contains 1 to 5% of methylbenzyl chloride depending on the average degree of chlorination and method of purification. This is seemingly an average quality of the technical-grade xylylene dichloride. Such a technical-grade xylylene dichloride can be used in the present process to achive the intended object. An insufficiently chlorinated product is rather preferred to an excessively chlorinated one because of easier removal of the former during the course of producing xylylene glycol according to this invention.

The alkali metal salts and alkaline earth metal salts of acetic acid for use in esterification according to this invention are sodium acetate, potassium acetate, and calcium acetate, etc. Of these, sodium acetate is preferred because, generally, it be used conveniently. A characteristic feature of the esterification in the present process is that it is carried out in the heterogeneous system in which the above-noted alkali acetate is suspended in an organic solvent containing xylylene dichloride dissolved therein. Accordingly, the alkali acetate is used in the form of neither aqueous solution nor finely ground powder but anhydrous small particles or flakes. When the alkali acetate contains water of crystallization, it should be previously converted into an anhydrous salt or should be used after having been heated in the esterification medium to remove the water of crystallization by distillation. The amount to be used of the alkali acetate is 2 mole-equivalents or more of the xylylene dichloride, a sufficient amount being usually 2.2 mole-equivalents. It is technically meaningless and uneconomical to use 2.5 mole-equivalents or more.

The solvent for use as a reaction medium for esterification can be any organic solvent so long as it is inert to the reaction and insoluble in water. Such solvents include aromatic hydrocarbons such as benzene, toluene, and xylene, and halogen-containing aromatic compounds such as monochlorobenzene, dichlorobenzene, and the like. It is preferable, however, to use a solvent having a boiling point of about 80° C to about 150° C. in view of maintaining the esterification temperature and recovery of the solvent. The amount to be used of the reaction medium is in the range from 50 to 200 parts for 100 parts by weight of xylylene dichloride. Since the rate of esterification in the present process becomes higher with the increase in concentration of xylylene dichloride, as will be explained later. It is preferable to use rather small amount of reaction medium. Too high a concentration of xylylene dichloride, however, is unsuitable because of much increased viscosity of the reaction mixture. From such a view-point, a desirable proportion of the reaction medium to xylylene dichloride is in the above-said range.

The tertiary amines to be used as the esterification catalyst are triethylamine, tri-n-propylamine, pyridine, hexamethylenetetramine, N,N'-dimethylpiperazine, N-methylpiperidine, N,N-dimethylaniline, N,N-dimethylbenzylamine, and N,N-diethylbenzylamine. The proportion of the catalyst to be used is about 0.5 to about 3, preferably 2, parts by weight for 100 parts by weight of xylylene dichloride.

The procedure for carrying out the process of this invention is explained below by taking as an example the case where p-xylylene dichloride is used as starting material.

p-Xylylene dichloride and anhydrous sodium acetate are weighed into a reactor. An inert organic solvent such as toluene is fed to the reactor and the reactor is heated to dissolve p-xylylene dichloride. After the temperature of the mixture is elevated to about 100° C. with stirring, a tertiary amine catalyst such as triethylamine is added dropwise to the mixture and the reaction is allowed to proceed at the same temperature, forming p-diacetoxymethylbenzene. In about 2 hours the esterification will be completed. The esterification temperature is preferably about 90° to 110° C., and when triethylamine is used as the catalyst, the temperature is preferably kept rather low so that the catalyst may not volatilize. As stated before, the esterification of the present process is allowed to start in a heterogeneous system comprising sodium acetate suspended in toluene containing dissolved p-xylylene dichloride and to complete in a heterogeneous system comprising toluene containing p-diacetoxymethylbenzene, which is formed, and suspended sodium chloride, which is a by-product separated out in solid form. Such precipitates of by-product sodium chloride can be easily removed by heating the reaction mixture at 50° to 60° C. and washing with hot water or filtering. In case the filtration is preferred, the sodium chloride crystals collected by filtration are washed with toluene, which is the same solvent as used in esterification, to recover the remaining p-diacetoxymethylbenzene. Although the toluene used in washing, even if in excess, affects little the succeeding saponification step, it is of course desirable to effect thorough washing with as small an amount of toluene as possible in view of recovery of the toluene. The catalyst is then recovered by washing with a mineral acid, preferably sulfuric acid. p-Diacetoxymethylbenzene is not necessarily isolated from the esterification mixture when saponification is succeedingly carried out. If desired, p-diacetoxymethylbenzene can be easily isolated by removing toluene by vacuum distillation from the toluene solution containing p-diacetoxymethylbenzene and freed from sodium chloride and the catalyst.

In the esterification step of the present process, the concentration of xylylene dichloride, a starting material, in the reactant mixture can be as high as 25 to 40% by weight and the reaction proceeds quantitatively, while in the case of conventional typical direct hydrolysis with an aqueous sodium carbonate solution, the optimum concentration of xylylene dichloride is usually about 5 to 8% by weight. According to the results of an experiment conducted by the present inventors on the conventional two-stage process, when p-xylylene dichloride of the concentration of 20% by weight is esterified with an aqueous sodium acetate solution, the esterification is not complete after 11 hours of reaction under reflux and the yield of intended p-diacetoxymethylbenzene is about 46%, with by products such as p-acetoxymethylbenzyl alcohol, a condensation product of the dibenzyl ether type and p-xylylene glycol. The rate of reaction of the conventional esterification by use of an aqueous sodium acetate solution increases with the decrease in concentration of p-xylylene dichloride in the reactant mixture, whereas in the present process the esterification time decreases with the increase in concentration of p-xylylene dichloride in the reactant mixture.

In the next stage of the present process, saponification of p-diacetoxymethylbenzene can be carried out by adding an alkali such as sodium hydroxide and water to the toluene solution containing p-diacetoxymethylbenzene and having been freed from sodium chloride and the catalyst, and allowing the reaction to proceed with stirring under reflux for 2 hours. The alkali for use in saponification can be any of the hydroxides, oxides, or carbonates of alkali metals or alkaline earth metals, without any particular restriction. From the viewpoint of practical convenience, sodium hydroxide is most suitable. The sufficient amount of alkali to be added is about 2.0 to 2.2 mole-equivalents to 1 mole-equivalent of p-diacetoxymethylbenzene. The amount of water to be added, though not critical, is preferably adjusted so that the final concentration of p-xylylene glycol in the aqueous layer may become about 10 to 20% by weight. Such a concentration of the reaction product is far higher as compared with conventional direct hydrolysis with an aqueous alkali solution. This means that the concentration of the alkali acetate, i.e. sodium acetate, formed in the aqueous layer is also high. The efficiency of extraction and recovery of p-xylylene glycol from an aqueous solution containing p-xylylene glycol and sodium acetate both in high concentrations may be expected to be increased by the salting-out effect. Moreover, since the impurities such as p-methylbenzyl alcohol is easily soluble in toluene, while p-xylylene glycol formed by saponification is easily soluble in water, it is convenient to remove the impurities.

After completion of the saponification, the aqueous layer containing p-xylylene glycol is neutralized and separated from the toluene layer. If it is necessary to remove impurities from the aqueous solution containing p-xylylene glycol, the impurities are extracted with an inert organic solvent. These impurities include p-methylbenzyl alcohol derived from p-methylbenzyl chloride contained in p-xylylene dichloride used as starting material. The organic solvent to be used is preferably the same solvent as used as the esterification medium because it does not dissolve p-xylylene glycol and it simplifies subsequent solvent recovery and other treatments. The extraction can be carried out either batchwise or continuously. The quantity of solvent to be used and the number of extractions can be suitably varied in accordance with the amount of impurities. The extraction temperature is preferably about 80° C. when toluene or monochlorobenzene is used as the extractant. The aqueous solution containing 10 to 20% by weight of p-xylylene glycol and having been freed from impurities by extraction is then subjected to the treatment for recovering p-xylylene glycol. If purified p-xylylene dichloride was used as starting material or if the quality of product p-xylylene glycol is not required to be of particularly high purity, the above-noted treatment for impurity removal can, of course, be omitted. When the impurity removal is unnecessary on account of low impurity content and a solvent which can dissolve relatively large amounts of xylylene glycol was used as the esterification medium, it is also possible to extract with water the xylylene glycol contained in the solvent layer which has been separated from the aqueous layer after saponification and to subject the aqueous extract together with said aqueous layer to the treatment for recovering the product xylylene glycol.

The extraction solvents for recovering p-xylylene glycol from the aqueous solution are preferably those polar solvents which are insoluble in water and have a large partition coefficient; the recommendable extractants include esters of lower fatty acids such as ethyl acetate, butyl acetates, and the like. The amount of the extractant to be used and the number of extractions are suitably selected so that the recovery of p-xylylene glycol may be effected substantially completely. The extraction can be carried out either batchwise or continuously. The extraction temperature is about 65° to 85° C. depending on the boiling point of the extractant. If it is desired to remove slight amounts of sodium acetate contained in the extract organic layer, the latter is washed with small amounts of water and the washings are separated by decantation. The separated washings are not discarded but possibly reused in the next extraction. The p-xylylene glycol in the extract solution is converted into a commercial product through such treatments as distillation to recover the solvent and vacuum drying.

Since the recovery of p-xylylene glycol in the present process is effected, as stated above, by extraction from an aqueous solution containing p-xylylene glycol and sodium acetate both in high concentrations, a high yield of the product can be secured owing partly to the salting-out effect of sodium acetate. When for example, the recovery operation is carried out batchwise, a recovery of 99% or higher is easily attained by extracting three times with ethyl acetate.

In the present process, the solvent, such as toluene or chlorobenzene, used as the esterification medium and the solvent, such as ethyl acetate, used as the extraction solvent for product recovery are recovered by distillation and reused. The exhausted aqueous solution remained after extraction of xylylene glycol from the aqueous layer obtained in the saponification step is evaporated to dryness to recover alkali acetate to be reused. Thus, the low material cost and the low level of waste except for sodium chloride or a solution thereof are among the advantageous features of the present process.

As stated in the foregoing, the present invention provides a process for producing xylylene glycol from xylylene dichloride, which is characterized by an ingeneous combination of operational steps such as esterification of xylylene dichloride, succeeding saponification, removal of impurities, and product recovery, which combination results in remarkable achievement.

As is apparent from the foregoing description, the advantages and merits of this invention may be listed as follows:

1. The esterification of xylylene dichloride used as starting material can be carried out at normal pressure and completed in a short period of time to obtain diacetoxymethylbenzene very easily.
2. During saponification, the side reaction with formation of a condensation product of the dibenzyl ether type is completely suppressed and, hence, the esterification and succeeding saponification proceed nearly quantitatively.
3. The esterification can be carried out with a high concentration of xylylene dichloride and so a correspondingly smaller reactor can be used.
4. After completion of esterification, a by-product inorganic chloride can easily be removed from the reaction mixture. The reaction mixture freed from the inorganic chloride and the catalyst can be used as such in the succeeding saponification step.
5. Since the xylylene glycol formed by saponification remains in the aqueous layer, while methylbenzene alcohol and other by-products remain in the organic layer, removal of impurities is easy, resulting in effective purification.

If it is required to further remove the impurities from the aqueous layer, the same solvent as used in esterification can be used, affording a commercial advantage.

6. The recovery of xylylene glycol can be accomplished in high yield by extraction from an aqueous solution containing xylylene glycol and sodium acetate both in high concentrations. Accordingly, heat-consuming and troublesome recovery procedures such as recrystallization are unnecessary.
7. Since xylylene glycol can be recovered, as stated above, by extraction from a highly concentrated solution, the product loss can be minimized and a high-quality xylylene glycol is obtained in a high yield.

The invention is illustrated below in detail with reference to Examples but the invention is not limited thereto. In Examples all parts are by weight unless otherwise indicated.

EXAMPLE 1

Into a four-neck flask provided with a reflux condenser, thermometer, dropping funnel, and stirrer, were charged 100 parts of p-xylylene dichloride (97.1% purity) containing p-methylbenzyl chloride and 102.5 parts of anhydrous sodium acetate. Into the flask was added 50 parts of toluene and heated to dissolve p-xylylene dichloride. To the resulting suspension, after having been heated with stirring to 100° C., was added dropwise 2 parts of triethylamine. The suspension was allowed to react at 98° to 103° C. for 2 hours. After completion of the reaction, the reaction mixture was cooled to 70° C. and filtered through a glass filter to remove the by-product sodium chloride. The sodium chloride crystals were washed with 100 parts of toluene at 50° C. To the combined toluene solution, was added 6.5 parts of 30-% sulfuric acid to remove the amine catalyst. After having been left standing, the aqueous sulfuric acid layer was drawn off. The toluene layer was placed in a four-neck flask provided with a reflux condenser, thermometer, and stirrer. To the toluene layer were added 46 parts of sodium hydroxide and 310 parts of water. The resulting mixture was allowed to undergo saponification at 87° to 88° C. for 2 hours. After completion of the saponification, the reaction mixture was neutralized with 3N hydrochloric acid and the mixture was left standing at 83° C. to allow the mixture to separate into two layers. After separation, there were obtained 475 parts of an aqueous layer containing 16.1% (as calculated) of p-xylylene glycol. To the aqueous layer was added 50 parts of toluene to extract impurities at 80° C. The extraction was repeated three times. After complete removal of impurities, the p-xylylene glycol contained in the aqueous layer was extracted at 65° C. three times with each the same quantity of ethyl acetate. There were obtained 1,330 parts of an ethyl acetate layer and 357 parts of an exhausted aqueous layer. The ethyl acetate layer was distilled in a rotary evaporator to remove ethyl acetate. The residue was dried in vacuo to obtain 72.8 parts of p-xylylene glycol in a yield of 95.0%. The p-xylylene glycol thus obtained was free from p-methylbenzyl alcohol (an impurity), as examined by gaschromatography, and had a melting of 115.7° – 116.7° C.

EXAMPLE 2

Esterification of p-xylylene dichloride (97.1% purity) was carried out under the same conditions as in Example 1, except that 125 parts of monochlorobenzene was used as saponification medium in place of 50 parts of toluene. After completion of the esterification, 250 parts of warmed water was added to the reaction mixture to dissolve precipitated sodium chloride, left standing at 80° C., and the chlorobenzene layer was drawn off. To the chlorobenzene layer, after having been freed from the amine catalyst by removing in the same manner as in Example 1, were added 48 parts of sodium hydroxide and 311 parts of water. The resulting mixture was allowed to undergo saponification at 94° C. for 2 hours. The reaction mixture was neutralized with 3N hydrochloric acid and left standing at 83° C. to effect gravity separation of the layers. To the aqueous layer containing p-xylylene glycol, was added 100 parts of chlorobenzene to extract impurities at 80° C. The mixture was left standing to effect separation and the aqueous layer was drawn off. The p-xylylene glycol contained in the aqueous layer was extracted with ethyl acetate in the same manner as in Example 1.

The exhausted aqueous layer was evaporated to dryness in a rotary evaporator and then further dehydrated at 70° C. under reduced pressure to recover anhydrous sodium acetate. The recovered sodium acetate was replenished with fresh sodium acetate equivalent in amount to the deficiency, and reused in the next esterification batch. The chlorobenzene and ethyl acetate which had been used in the experiment were also recovered by distillation and reused in the next reaction and extraction. The results of repeated experiments by use of successively recovered materials were as shown in Table 1, from which it is apparent that repeated reuse of the materials has no adverse effect.

Table 1

| Number of repeated experiments | p-Xylylene glycol | | |
|---|---|---|---|
| | Yield (%) | p-Methylbenzyl alcohol content (%) | Melting point (° C.) |
| 1 | 94.6 | < 0.1 | 115.5 – 116.0 |
| 2 | 95.6 | Trace | 115.4 – 116.1 |
| 5 | 94.7 | 0 | 116.0 – 116.5 |

EXAMPLE 3

Into a four-neck flask provided with a reflux condenser, thermometer, dropping funnnel, and stirrer, were charged 40 parts of o-xylylene dichloride of 99.8% purity, 40 parts of anhydrous sodium acetate, and 20 parts of monochlorobenzene. Into the flask was added with stirring at 100° C., 0.8 part of triethylamine. Esterification was allowed to proceed at 97° to 101° C. for 10 hours. To the reaction mixture was added 100 parts of warm water to dissolve the by-product sodium chloride. The mixture was left standing to allow it to settle in monochlorobenzene layer and aqueous layer. To the monochlorobenzene layer which had been freed from the catalyst amine by removing with 2.6 parts of 30-% sulfuric acid, were added 19.4 parts of sodium hydroxide and 170 parts of water. Saponification was allowed to proceed at 94° C. for 2 hours. After saponification, the reaction mixture was neutralized with 3N hydrochloric acid and left standing at 85° C. to allow the mixture to settle in two layers. Without having been freed from impurities, the aqueous layer containing o-xylylene glycol was extracted three times with ethyl acetate in a manner similar to that in Example 1. The ethyl acetate extracts were combined, distilled to recover ethyl acetate, and dried in vacuo to obtain 29.6 parts of o-xylylene glycol (melting point, 60.7° – 62° C.) in a yield of 94.0%.

EXAMPLE 4

In a manner similar to that in Example 1, m-xylylene dichloride was converted into m-diacetoxymethylbenzene at 97° to 101° C. in 3 hours by use of a reactant mixture comprising 100 parts of m-xylylene dichloride (97.6% purity), 100 parts of anhydrous sodium acetate, 125 parts of monochlorobenzene, and 2 parts of triethylamine. To the reaction mixture was added 250 parts of warm water to dissolve the by-product sodium chloride. The mixture was left standing at 80° C. to allow it to settle in two layers. To the monochlorobenzene layer which had been freed from the catalyst amine by removing in the same manner as in Example 1, were added 46 parts of sodium hydroxide and 310 parts of water to allow the saponification to proceed at 94° C. for 2 hours. After saponification, the reaction mixture was neutralized with 3N hydrochloric acid and left standing at 82° C. to allow the mixture to settle in two layers. The aqueous layer containing m-xylylene glycol, was added at 80° C. 50 parts of monochlorobenzene to extract impurities. After separation, m-xylylene glycol was extracted from the purified aqueous layer with n-butyl acetate in the same way as in Example 1. The n-butyl acetate layers obtained by repeating batchwise extraction three times were combined, distilled to recover ethyl acetate, and dried in vacuo to obtain 76.0 parts of m-xylylene glycol (melting point, 53.5° – 55° C.) in a yield of 98.7%.

What is claimed is:

1. In the process for producing a xylylene glycol which comprises reacting a xylylene dichloride with an alkali metal or alkaline earth metal salt of acetic acid in the presence of a catalyst consisting of a tertiary amine in an inert organic solvent to effect esterification, removing the by-product inorganic chloride and the catalyst from the resulting diacetoxymethylbenzene solution and then saponifying the diacetoxymethylbenzene with an aqueous alkali solution to obtain the corresponding xylylene glycol, the improvement comprising using as said inert organic solvent at least one member selected from the group consisting of benzene, toluene, xylene and monochlorobenzene, separating the reaction liquid after the completion of saponification into an aqueous solution layer containing the xylylene glycol formed and a solvent layer, and recovering the xylylene glycol from said aqueous solution layer with at least one extraction solvent selected from the group consisting of ethyl acetate and n-butyl acetate.

2. The process of claim 1 wherein the alkali metal or alkaline earth metal salt of acetic acid is employed in an amount of 2 to 2.5 mole equivalents per mole equivalent of xylylene dichloride.

3. A process according to claim 1, wherein the extraction of the xylylene glycol is carried out at the concentration of the xylylene glycol in the aqueous solution layer of 10 to 20% by weight.

4. The process of claim 1 wherein there is used 50 to 200 parts of organic solvent per 100 parts of xylylene dichloride in producing the xylylene glycol.

5. The process of claim 4, wherein the esterification is carried out at 90° to 110° C.

6. The process of claim 4 wherein the alkali used for saponification is present in an amount of 2.0 to 2.2 mole equivalents per mole equivalent of xylylene dichloride.

7. The process of claim 4 wherein the tertiary amine is triethylamine, tri-n-propylamine, pyridine, hexamethylenetetramine, N,N'-dimethylpiperazine, N-methylpiperidine, N,N-dimethylaniline, N,N-dimethylbenzyllamine or N,N-diethylbenzylamine.

8. The process of claim 7 wherein the tertiary amine is triethylamine, N,N'-dimethylpiperazine- N-methylpiperidine or N,N-dimethylbenzylamine.

9. The process of claim 8 wherein the amine is triethylamine.

* * * * *